US010617285B2

(12) United States Patent
Igarashi (10) Patent No.: US 10,617,285 B2
(45) Date of Patent: Apr. 14, 2020

(54) IMAGING MODULE WITH MULTI-LAYER SUBSTRATE AND ENDOSCOPE APPARATUS

(71) Applicant: OLYMPUS CORPORATION, Tokyo (JP)

(72) Inventor: Takatoshi Igarashi, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 409 days.

(21) Appl. No.: 15/082,016

(22) Filed: Mar. 28, 2016

(65) Prior Publication Data

US 2016/0206186 A1 Jul. 21, 2016

Related U.S. Application Data

(63) Continuation of application No. PCT/JP2014/070249, filed on Jul. 31, 2014.

(30) Foreign Application Priority Data

Sep. 30, 2013 (JP) ................................. 2013-204884

(51) Int. Cl.
*A61B 1/05* (2006.01)
*A61B 1/00* (2006.01)
*A61B 1/06* (2006.01)

(52) U.S. Cl.
CPC ............ *A61B 1/051* (2013.01); *A61B 1/0008* (2013.01); *A61B 1/00018* (2013.01);
(Continued)

(58) Field of Classification Search
CPC ... A61B 1/051; A61B 1/0008; A61B 1/00114; A61B 1/05; A61B 1/0676; A61B 1/00096; A61B 1/00018; A61B 1/00101
(Continued)

(56) References Cited

U.S. PATENT DOCUMENTS 4,622,580 A * 11/1986 Levine .............. H01L 31/02005
257/228
4,831,456 A 5/1989 Takamura
(Continued)

FOREIGN PATENT DOCUMENTS

JP S63-272180 A 11/1988
JP H04-218136 A 8/1992
(Continued)

OTHER PUBLICATIONS

International Search Report dated Nov. 11, 2014 issued in PCT/JP2014/070249.

*Primary Examiner* — Timothy J Neal
*Assistant Examiner* — William B Chou
(74) *Attorney, Agent, or Firm* — Scully, Scott, Murphy & Presser PC (57) ABSTRACT

An imaging module includes: an image sensor; a substrate having a conductor layer and extending from the image sensor; a multi-layer substrate having therein conductor layers on the substrate; electronic components mounted on/in the multi-layer substrate; an image signal electrode pad and a drive signal electrode pad on the image sensor; an image signal cable; a drive signal cable; an image signal wiring pattern through which an image signal is transmitted from the image signal electrode pad to the image signal cable; and a drive signal wiring pattern through which a drive signal is transmitted from the drive signal cable to the drive signal electrode pad. At least one of the electronic components is embedded inside the multi-layer substrate. The image signal wiring pattern and the drive signal wiring pattern are separated into different conductor layers of the substrate and the multi-layer substrate due to the embedded electronic component.

13 Claims, 8 Drawing Sheets

(52) U.S. Cl.
CPC ............ *A61B 1/00114* (2013.01); *A61B 1/05* (2013.01); *A61B 1/00096* (2013.01); *A61B 1/0676* (2013.01)

(58) Field of Classification Search
USPC ....... 600/109, 110, 112, 128, 129, 130, 132, 600/140, 160
See application file for complete search history.

(56) References Cited

U.S. PATENT DOCUMENTS

| | | | | |
|---|---|---|---|---|
| 4,895,138 | A * | 1/1990 | Yabe | A61B 1/05 348/E5.027 |
| 5,220,198 | A | 6/1993 | Tsuji | |
| 6,796,939 | B1 * | 9/2004 | Hirata | A61B 1/00036 600/109 |
| 7,549,958 | B2 * | 6/2009 | Hirata | A61B 1/0676 439/86 |
| 8,308,637 | B2 * | 11/2012 | Ishigami | A61B 1/00177 600/129 |
| 2009/0012358 | A1 * | 1/2009 | Ichihashi | A61B 1/00105 600/110 |
| 2010/0202126 | A1 * | 8/2010 | Nakamura | H01L 25/0657 361/803 |
| 2013/0168740 | A1 * | 7/2013 | Chen | B81C 1/00238 257/254 |

FOREIGN PATENT DOCUMENTS

| | | |
|---|---|---|
| JP | 2001-257937 A | 9/2001 |
| JP | 2011-050497 A | 3/2011 |

* cited by examiner

IMAGING MODULE WITH MULTI-LAYER SUBSTRATE AND ENDOSCOPE APPARATUS

CROSS-REFERENCE TO RELATED APPLICATIONS

This application is a continuation of PCT international application Ser. No. PCT/JP2014/070249 filed on Jul. 31, 2014 which designates the United States, incorporated herein by reference, and which claims the benefit of priority from Japanese Patent Application No. 2013-204884, filed on Sep. 30, 2013, incorporated herein by reference.

BACKGROUND

1. Technical Field

The disclosure relates to an imaging module and an endoscope apparatus, the imaging module being provided at a distal end of an insertion unit of an endoscope that is configured to be inserted into a subject to image the inside of the subject.

2. Related Art

Endoscope apparatuses have been widely used to perform various examinations in a medical field and an industrial field. Among those apparatuses, a medical endoscope apparatus is widely used because an in-vivo image of a body cavity can be acquired without making an incision on a subject such as a patient by inserting an elongated, flexible insertion unit provided with an image sensor at a distal end thereof into the body cavity of the subject and, at the same time, a curative treatment can be performed as needed by projecting a treatment tool from the distal end of the insertion unit.

Fitted to the distal end of the insertion unit of such endoscope apparatus is an imaging unit having the image sensor and a circuit board populated with electronic components such as a capacitor and an IC chip constituting a drive circuit of the image sensor, where a signal cable is soldered to the circuit board of the imaging unit. The imaging unit is adapted such that an image signal output from the image sensor is output to an image signal cable through a buffer chip while a drive signal is input to the image sensor from a drive signal cable where, as the imaging unit is reduced in size, a drive signal transmission path and an image signal transmission path are arranged close to each other in the substrate so that there has been a possibility of the drive signal interfering with the image signal to generate noise in an image.

As a technique of reducing the influence of crosstalk, there is proposed an imaging apparatus in which a wiring pattern transmitting a different electrical signal is interposed between a wiring pattern of the image signal output from a solid state image sensor on the circuit board and a wiring pattern of the drive signal (refer to Japanese Patent Application No. 2001-257937, for example).

Moreover, as a similar technique, there is proposed an imaging apparatus which includes an image sensor, a first circuit board and a second circuit board, and in which a power supply wiring pattern is formed at a predetermined distance away from an image signal wiring pattern and a drive signal wiring pattern (refer to Japanese Patent Application No. 2011-50497, for example).

SUMMARY

In some embodiments, an imaging module includes: a solid state image sensor having a light-receiving surface and configured to receive light and to perform photoelectric conversion on the received light to generate an electrical signal; a substrate having a conductor layer and extending from the solid state image sensor in a direction opposite to where the light-receiving surface is provided, along an optical axis direction of the solid state image sensor; a multi-layer substrate on a surface of the substrate, the multi-layer substrate having therein a plurality of conductor layers and a plurality of via holes; a plurality of electronic components mounted on or in the multi-layer substrate; an image signal electrode pad on the solid state image sensor; a drive signal electrode pad on the solid state image sensor; an image signal cable for transmitting an image signal; a drive signal cable for transmitting a drive signal; an image signal wiring pattern through which the image signal is transmitted from the image signal electrode pad to the image signal cable; and a drive signal wiring pattern through which the drive signal is transmitted from the drive signal cable to the drive signal electrode pad. At least one of the plurality of electronic components is embedded inside the multi-layer substrate. The image signal wiring pattern and the drive signal wiring pattern are separated on a side of the solid state image sensor into different conductor layers of the substrate and the multi-layer substrate due to the at least one of the plurality of electronic components embedded inside the multi-layer substrate, thereby to allow the image signal and the drive signal to be transmitted to the image signal cable and the drive signal electrode pad, respectively, through the different conductor layers of the substrate and the multi-layer substrate.

In some embodiments, an endoscope apparatus includes an insertion unit, at a distal end of which the imaging module is provided.

The above and other features, advantages and technical and industrial significance of this invention will be better understood by reading the following detailed description of presently preferred embodiments of the invention, when considered in connection with the accompanying drawings.

DETAILED DESCRIPTION

As modes for carrying out the invention (hereinafter referred to as "embodiment(s)"), an endoscope apparatus having an imaging module will be described below. The present invention is not to be limited by the embodiments. The same reference signs are used to designate the same elements throughout the drawings. The drawings being provided schematically, one needs to further keep in mind that the relationship between the thickness and width of each member as well as a ratio of each member are different from actual ones. The dimension and ratio of some parts are different among the drawings.

First Embodiment

Figure 1:
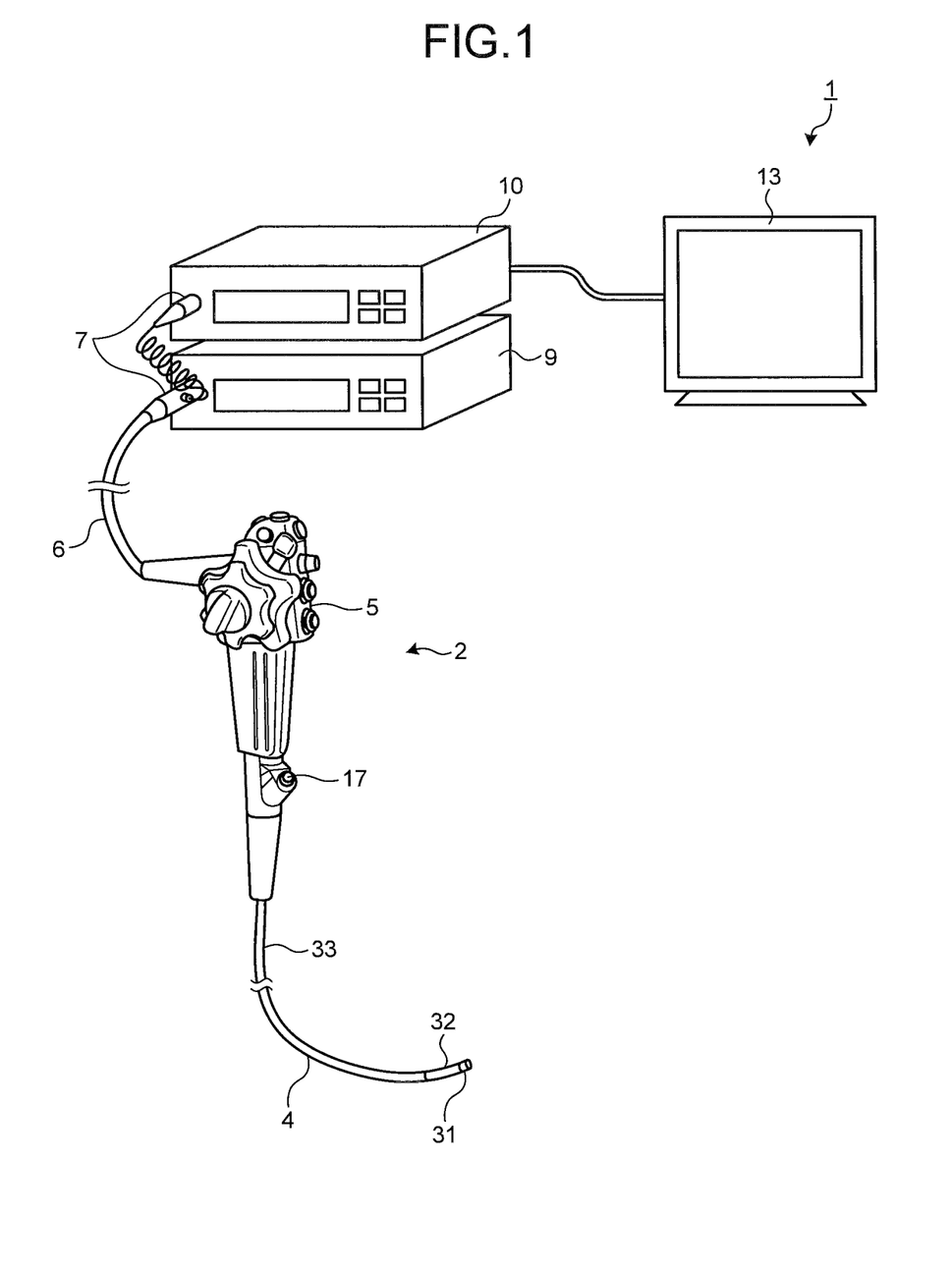
FIG. 1 is a diagram schematically illustrating an overall configuration of an endoscope system according to a first embodiment of the present invention.

FIG. 1 is a diagram schematically illustrating an overall configuration of an endoscope system according to a first embodiment of the present invention. As illustrated in FIG. 1, an endoscope apparatus 1 includes an endoscope 2, a universal cord 6, a connector 7, a light source device 9, a processor (control device) 10, and a display device 13.

The endoscope 2 images an in-vivo image of a subject by inserting an insertion unit 4 into a body cavity of the subject and outputs an imaging signal. An electric cable bundle inside the universal cord 6 extends to a distal end of the insertion unit 4 of the endoscope 2 and is connected to an imaging apparatus provided at a distal end portion 31 of the insertion unit 4.

The connector 7 is provided at a proximal end of the universal cord 6 and connected to the light source device 9 and the processor 10 to perform predetermined signal processing on an imaging signal output by the imaging apparatus at the distal end portion 31 connected to the universal cord 6, perform analog-digital conversion (A/D conversion) on the imaging signal, and output the signal as an image signal.

The light source device 9 is formed of a white LED, for example. Pulsed white light illuminated by the light source device 9 passes through the connector 7 and the universal cord 6 to become illumination light radiated from the distal end of the insertion unit 4 of the endoscope 2 toward a subject.

The processor 10 performs predetermined image processing on the image signal output from the connector 7 and controls the entire endoscope apparatus 1. The display device 13 displays the image signal processed by the processor 10.

An operating unit 5 provided with various buttons and knobs to operate an endoscopic function is connected to a proximal end side of the insertion unit 4 of the endoscope 2. The operating unit 5 is provided with a treatment tool insertion port 17 from which a treatment tool such as forceps, an electric knife, or an examination probe is inserted into the body cavity of the subject.

The insertion unit 4 is formed of the distal end portion 31 provided with the imaging apparatus, a bend portion 32 that is continuously connected to a proximal end side of the distal end portion 31 and freely bent in a plurality of directions, and a flexible tube 33 that is continuously connected to a proximal end side of the bend portion 32. The bend portion 32 is bent by an operation on a bend operation knob provided in the operating unit 5, and is freely bent in four directions including upward, downward, left and right directions according to traction and slackening of a bend wire inserted through the interior of the insertion unit 4.

A light guide bundle (not shown) transmitting the illumination light from the light source device 9 is arranged in the endoscope 2, and an illumination lens (not shown) is arranged at an end to which the illumination light from the light guide bundle is emitted. The illumination lens is provided at the distal end portion 31 of the insertion unit 4 so that the illumination light is radiated toward the subject.

Figure 2:
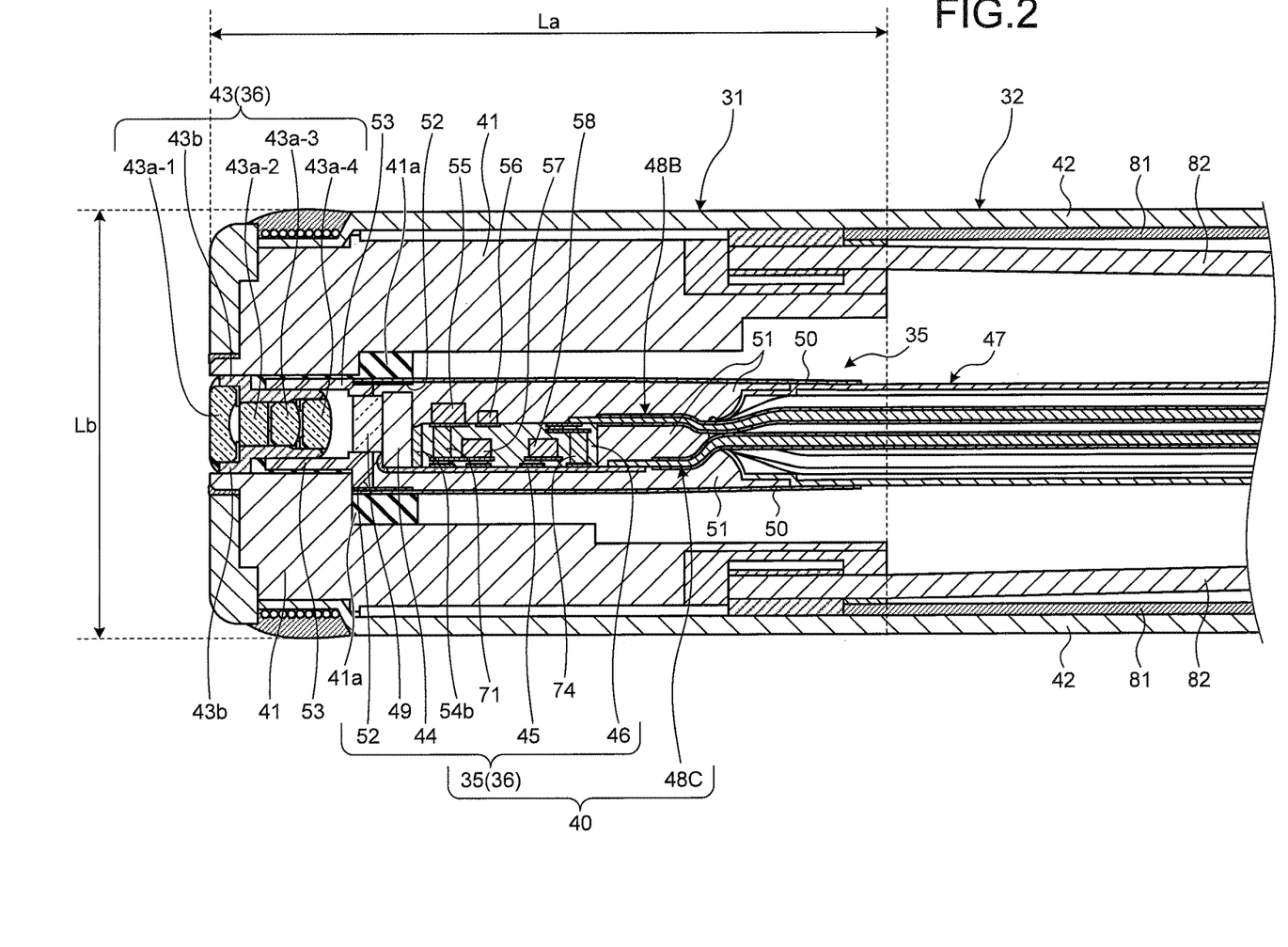
FIG. 2 is a partial cross-sectional view of a distal end of the endoscope illustrated in FIG. 1.

Next, the configuration of the distal end portion 31 of the endoscope 2 will be described in detail. FIG. 2 is a partial cross-sectional view of the distal end of the endoscope 2. FIG. 2 is a cross-sectional view obtained when the distal end is sectioned by a plane orthogonal to a substrate surface of an imaging module provided at the distal end portion 31 of the endoscope 2 and parallel to an optical axis direction of the imaging module. FIG. 2 illustrates the distal end portion 31 and a part of the bend portion 32 of the insertion unit 4 of the endoscope 2.

As illustrated in FIG. 2, the bend portion 32 is freely bent in the four directions including the upward, downward, left and right directions according to traction and slackening of a bend wire 82 inserted through the interior of a bend tube 81 that is arranged on the inner side of a cover tube 42 to be described. An imaging apparatus 36 is provided inside the distal end portion 31 extending on the distal end side of the bend portion 32.

The imaging apparatus 36 includes a lens unit 43 and an imaging unit 35 arranged on the proximal end side of the lens unit 43, and adheres to the inner side of a distal end body 41 by an adhesive 41a. The distal end body 41 is made of a rigid member that forms an inner space accommodating the imaging unit 35. The outer periphery of the proximal end of the distal end body 41 is covered by the flexible cover tube 42. A member arranged on the proximal end side relative to the distal end body 41 is formed of a flexible member to allow the bend portion 32 to be bendable. The distal end portion 31 where the distal end body 41 is arranged corresponds to a rigid portion of the insertion unit 4. A length La of the rigid portion corresponds to the length from the distal end of the insertion unit 4 to the proximal end of the distal end body 41. Note that a length Lb corresponds to an outer diameter of the distal end of the insertion unit 4.

The lens unit 43 includes a plurality of objective lenses 43a-1 to 43a-4 and a lens holder 43b holding the objective lenses 43a-1 to 43a-4, where a distal end of the lens holder 43b is fixed to the distal end body 41 by fitted and fixed to the interior of the distal end body 41.

The imaging unit 35 includes a solid state image sensor 44 such as a CCD or CMOS having a light-receiving surface that receives light on the surface, a substrate 45 extending from the solid state image sensor 44, a multi-layer substrate 46 populated with electronic components 55 to 58 constituting a drive circuit of the solid state image sensor 44, and a glass lid 49 adhering to the solid state image sensor 44 while covering the light-receiving surface of the solid state image sensor 44. An imaging module 40 includes the imaging apparatus 36 having the lens unit 43 and the imaging unit 35, a drive signal cable 48A electrically connected to the solid state image sensor 44 to drive the solid state image sensor 44, an image signal cable 48B for transmitting an image signal output from the solid state image sensor 44, and a plurality of power supply cables 48C for supplying power to the solid state image sensor 44 and the electronic components 55 to 58.

Proximal ends of the drive signal cable 48A, the image signal cable 48B, and the power supply cable 48C are put together into an electric cable bundle 47 and extend toward the proximal end of the insertion unit 4. The electric cable bundle 47 is inserted/arranged in the insertion unit 4 and extends up to the connector 7 through the operating unit 5 and the universal cord 6 illustrated in FIG. 1.

A subject image formed by the objective lenses 43*a*-1 to 43*a*-4 of the lens unit 43 is detected by the solid state image sensor 44 arranged at image-forming positions of the objective lenses 43*a*-1 to 43*a*-4 and converted into the image signal.

The solid state image sensor 44 adheres to the substrate 45 and the multi-layer substrate 46 by an adhesive 54*b*. The solid state image sensor 44 and the connection between the solid state image sensor 44 and the substrate 45 are covered by a metallic reinforcing member 52. In order to prevent the influence of external static electricity on the electronic components 55 to 58 on the substrate 45, the reinforcing member 52 is disposed away from the solid state image sensor 44, the substrate 45 and the multi-layer substrate 46.

An outer periphery of a distal end portion of each of the imaging unit 35 and the electric cable bundle 47 is covered by a heat-shrinkable tube 50 in order to increase tolerance. An adhesive resin 51 fills a gap among components inside the heat-shrinkable tube 50.

A solid state image sensor holder 53 holds the solid state image sensor 44 adhering to the glass lid 49 by fitting an outer peripheral surface of the glass lid 49 into an inner peripheral surface on the proximal end side of the solid state image sensor holder 53. An outer peripheral surface on the proximal end side of the solid state image sensor holder 53 is fitted to an inner peripheral surface on the distal end side of the reinforcing member 52. An outer peripheral surface on the proximal end side of the lens holder 43*b* is fitted to an inner peripheral surface on the distal end side of the solid state image sensor holder 53. While each member is fitted in this manner, the outer peripheral surface of the lens holder 43*b*, the outer peripheral surface of the solid state image sensor holder 53 and an outer peripheral surface on the distal end side of the heat-shrinkable tube 50 are fixed to an inner peripheral surface of the distal end of the distal end body 41 by the adhesive 41*a*.

Figure 3:
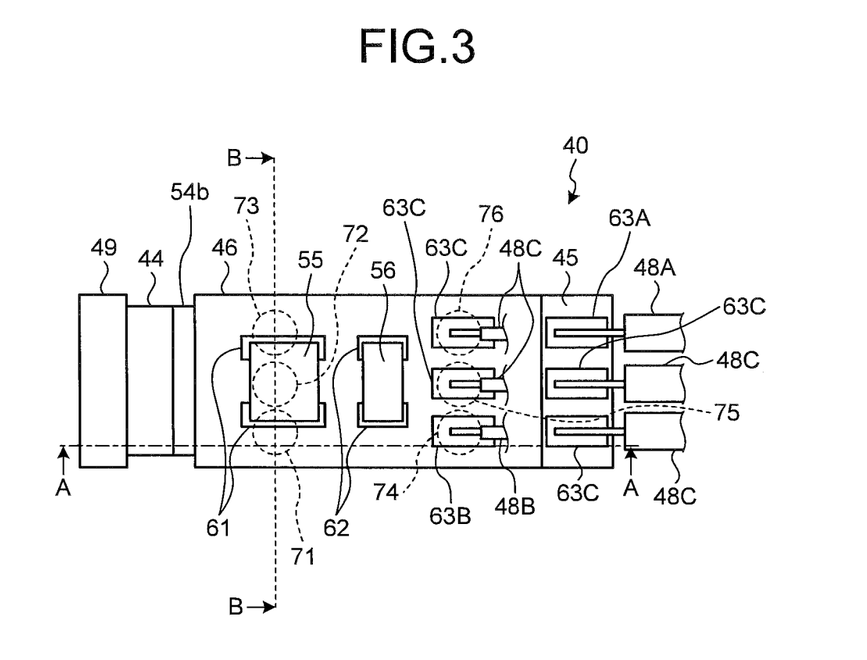
FIG. 3 is a plan view of an imaging module illustrated in FIG. 2 as seen in plan view along a layered direction.
Figure 4:
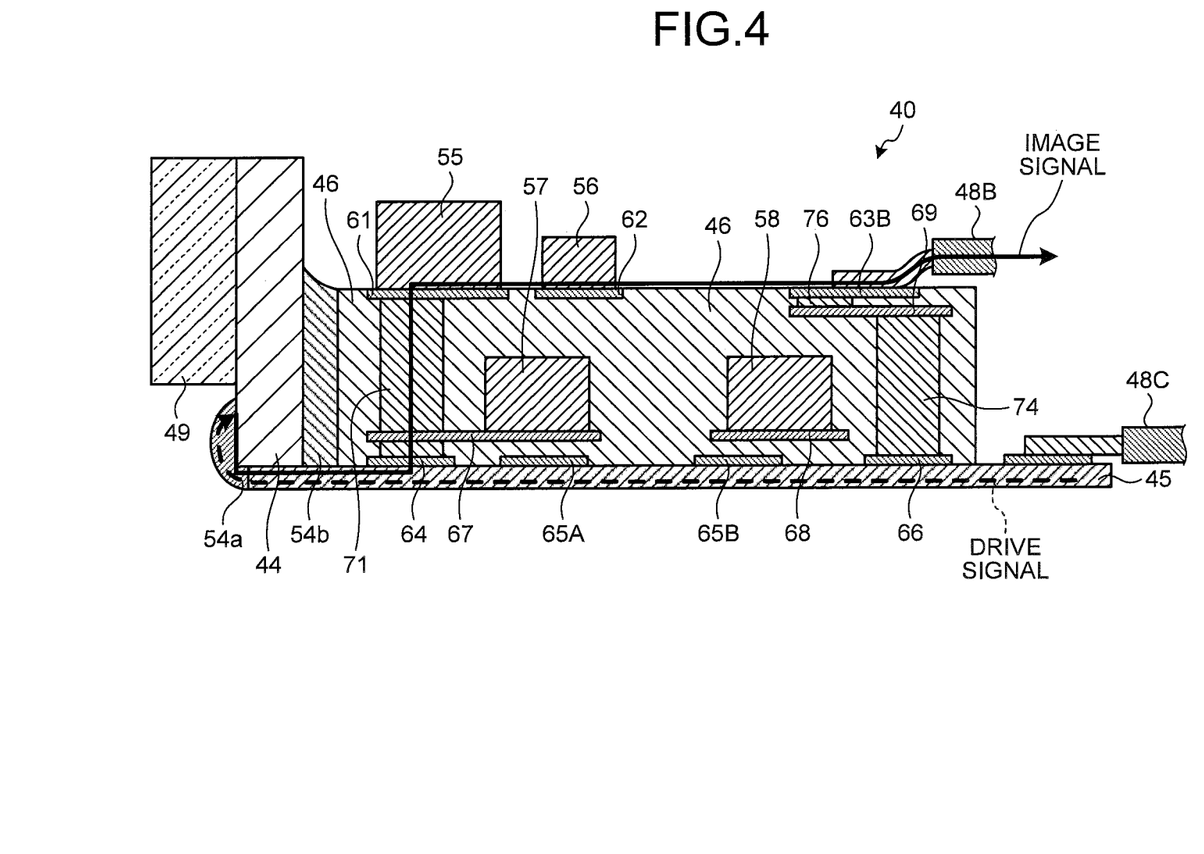
FIG. 4 is a cross-sectional view taken along line A-A of FIG. 3.
Figure 5:
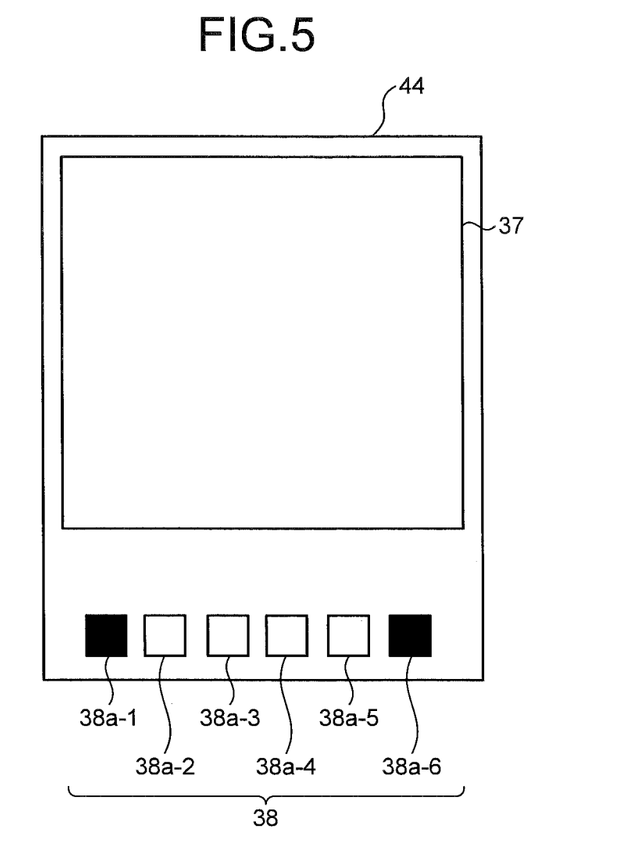
FIG. 5 is a front view of a light-receiving surface of a solid state image sensor illustrated in FIG. 2.

The imaging module 40 will now be described. FIG. 3 is a plan view of the imaging module 40 as seen in plan view along a layered direction. FIG. 4 is a cross-sectional view taken along line A-A of FIG. 3 and obtained when the imaging module 40 is sectioned by a plane perpendicular to the surface of the substrate 45 and parallel to an optical axis direction of the solid state image sensor 44. FIG. 5 is a front view of the light-receiving surface of the solid state image sensor 44 and illustrates a configuration of an electrode pad formed at the bottom of the solid state image sensor 44.

As illustrated in FIG. 5, the solid state image sensor 44 includes a light-receiving unit 37 and an electrode pad 38 that are formed on the side of the light-receiving surface, where a plurality of pixel units is arranged in a two-dimensional matrix in the light-receiving unit. The electrode pad 38 includes a drive signal electrode pad 38*a*-1, power supply signal electrode pads 38*a*-2 to 38*a*-5, and an image signal electrode pad 38*a*-6 where the drive signal electrode pad 38*a*-1 and the image signal electrode pad 38*a*-6 are arranged to be farthest apart from each other. Each electrode pad 38 is electrically connected to an inner lead (not shown) of the substrate 45 and covered by a sealing resin 54*a* so that the solid state image sensor 44 and the substrate 45 are connected.

The substrate 45 is a flexible printed circuit board and extends from the solid state image sensor 44 toward the optical axis direction on the side opposite to the light-receiving surface of the solid state image sensor 44. The multi-layer substrate 46 in which a plurality of layers is layered is formed on the surface of the substrate 45. The multi-layer substrate 46 is electrically and mechanically connected to a conductor layer (not shown) of the substrate 45.

Among a plurality of electronic components constituting a drive circuit of the solid state image sensor 44, one or more electronic components are mounted on a top surface of the multi-layer substrate 46 while one or more electronic components are embedded and mounted inside the substrate. FIGS. 3 and 4 illustrate an example where, among the plurality of electronic components 55 to 58, the two electronic components 55 and 56 are mounted on the top surface of the multi-layer substrate 46. Also, among the plurality of electronic components 55 to 58, the two electronic components 57 and 58 are embedded inside the multi-layer substrate 46. Note that it is preferable to adopt a CMOS image sensor where the solid state image sensor 44 functions as a first chip including at least the light-receiving unit 37 and a read unit reading an imaging signal subjected to photoelectric conversion by the light-receiving unit 37 while the electronic component 55 has a function as a second chip including at least a transmission buffer. If the CMOS image sensor including the first chip and the second chip is employed, the solid state image sensor 44 as the first chip and the electronic component 55 as the second chip can be separated at a predetermined distance from each other so that a dark current arising from heating of the second chip can be reduced to prevent degradation in image quality.

Moreover, in order to decrease a mounting area, the electronic component 55 as the second chip is mounted on the multi-layer substrate 46 by flip-chip mounting using a gold bump and is thus preferably arranged on any via hole to be described. A high load applied from a top surface of the electronic component 55 when performing the flip-chip mounting deforms the multi-layer substrate 46 in some cases. Connection of the embedded electronic components 57 and 58 may possibly be unstable or destructed when the multi-layer substrate 46 is deformed, so that it is preferable to arrange the electronic component 55 on the via hole in order to prevent the deformation of the multi-layer substrate 46 caused by the load applied in the flip-chip mounting. The electronic component 55 as the second chip can also be mounted on the multi-layer substrate 46 by a solder ball. Likewise, a load is generated when the image signal cable 48B and the power supply cable 48C are connected to cable connection lands 63B and 63C so that, for the purpose of preventing the deformation of the multi-layer substrate 46 caused by the load, the cable connection lands 63B and 63C are preferably arranged on via holes as well.

Figure 6:
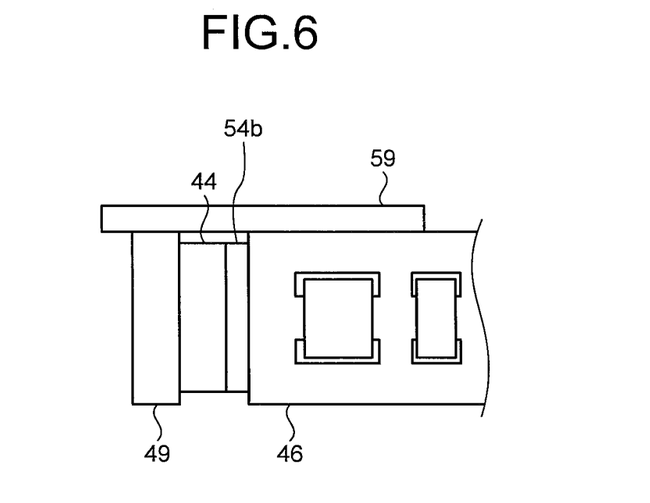
FIG. 6 is a diagram illustrating an example of a reinforcing portion of an image sensor.

The whole imaging module 40 including the substrate 45, the multi-layer substrate 46, the electronic components 55 and 56, the drive signal cable 48A, the image signal cable 48B and the power supply cable 48C is arranged to be accommodated within a projected area obtained by projecting the solid state image sensor 44 in the optical axis direction. Moreover, the glass lid 49 and/or the solid state image sensor 44 are/is flush with at least one of left and right side faces of the multi-layer substrate 46. The glass lid 49 and/or the solid state image sensor 44 are/is flush with at least one of left and right side faces of the multi-layer substrate 46, so that the imaging module 40 can be gripped easily when reduced in size. Moreover, as illustrated in FIG. 6, a plate-shaped reinforcing portion 59 may be joined to the flush surface by an adhesive. The formation of the reinforcing portion 59 makes gripping easy while at the same time the adhesive joining the reinforcing portion 59 can further increase connection strength among the glass lid 49, the solid state image sensor 44 and the multi-layer substrate 46.

Formed on the multi-layer substrate 46 are two connection lands 61 to which the electronic component 55 is electrically connected, two connection lands 62 to which the electronic component 56 is connected, and the cable connection lands 63B and 63C to which conductors at distal ends of the image signal cable 48B and the power supply cable 48C are electrically and mechanically connected. Formed on the substrate 45 are cable connection lands 63A and 63C to which conductors at distal ends of the drive signal cable 48A and the power supply cable 48C are electrically and mechanically connected, and a connection land (not shown) connected to the multi-layer substrate 46. In the example illustrated in FIG. 3, the cable connection land 63A for the drive signal cable 48A, the cable connection land 63B for the image signal cable 48B and the four cable connection lands 63C for the power supply cables 48C are provided, where the drive signal cable 48A, the image signal cable 48B, and the power supply cables 48C can be connected to the cable connection lands 63A, 63B, and 630, respectively through solder or the like. A plurality of connection lands 64, 65A, 65B and 66 electrically connected to the substrate 45 is formed on a bottom surface of the multi-layer substrate 46. The multi-layer substrate 46 is preferably a resin substrate, particularly a multi-layer resin substrate in which multiple resin layers using thermoplastic resin are stacked, but may also be a ceramic substrate with an electronic component mounted in a recess portion on the substrate.

A plurality of conductor layers is layered inside the multi-layer substrate 46. Conductor layers 67, 68 and 69 are illustrated in the cross section in FIG. 4. Moreover, a plurality of via holes 71 to 76 is formed inside the multi-layer substrate 46. Each of the conductor layers 67, 68 and 69 is electrically connected to any of the plurality of via holes 71 to 76. In the first embodiment, among the via holes 71 to 73 closest to the solid state image sensor 44, the via hole 71 arranged at the shortest distance from the cable connection land 63B to which the image signal cable 48B is connected functions as a first via hole.

In the first embodiment, as indicated with a solid line in FIG. 4, an image signal is transmitted from the image signal electrode pad 38a-6 of the solid state image sensor 44 to the substrate 45 through the inner lead and then transmitted to the electronic component 55 mounted on the surface of the multi-layer substrate 46 through the connection land 64, the via hole 71, and the connection land 61. The image signal is amplified by the electronic component 55 and thereafter output to the processor 10 via the image signal wiring pattern, the cable connection land 63B and the image signal cable 48B on the multi-layer substrate 46. The image signal output from the image signal electrode pad 38a-6 is weak and susceptible to the influence of noise, but image noise caused by crosstalk from the drive signal is less likely to occur because the image signal is input and amplified to/by the electronic component 55 having the transmission buffer on the surface of the multi-layer substrate 46 in the shortest distance through the first via hole, namely the via hole 71, that is closest to the solid state image sensor 44 and closest in plan view to the image signal electrode pad 38a-6. In order to reduce the influence of noise, it is preferable that the image signal wiring pattern is formed linearly (to be short in length).

On the other hand, as indicated with a dotted line in FIG. 4, a drive signal input from the drive signal cable 48A is input to the drive signal electrode pad 38a-1 through the cable connection land 63A and the drive signal wiring pattern. The drive signal is input to the solid state image sensor 44 only through the substrate 45 and transmitted through a layer different from the image signal (the image signal is mainly transmitted on the multi-layer substrate 46 while the drive signal is transmitted on the substrate 45). In order to reduce the influence of noise, it is preferable that the drive signal wiring pattern is also formed linearly (to be short in length). The first embodiment can reduce the influence of crosstalk from the drive signal on the weak signal before it is input to the transmission buffer, because the image signal output through the image signal electrode pad 38a-6 formed at the bottom of the solid state image sensor 44 and the drive signal input to the drive signal electrode pad 38a-1 are separated on the side of the solid state image sensor 44 for transmission due to the electronic components 57 and 58 embedded inside the multi-layer substrate 46. Moreover, the drive signal being transmitted only on the substrate 45, a via hole for transmitting the drive signal need not be formed in the multi-layer substrate 46 so that the imaging module 40 can be reduced in size.

Figure 7:
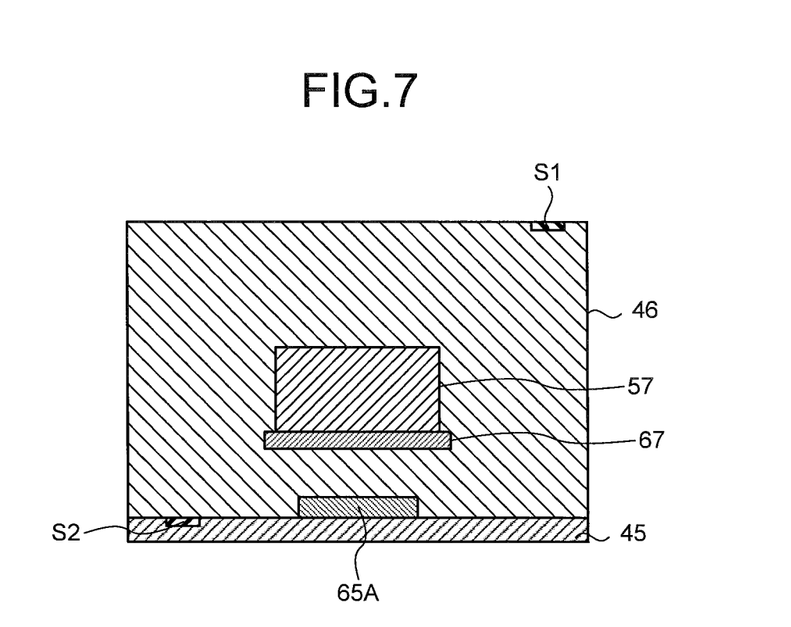
FIG. 7 is a cross-sectional view taken along line B-B of FIG. 3.

FIG. 7 is a cross-sectional view taken along line B-B of FIG. 3 where, in the first embodiment, the image signal wiring pattern is formed on a right side (S1) on the surface of the multi-layer substrate 46 while the drive signal wiring pattern is formed on a left side (S2) on the substrate 45. As illustrated in the cross section of the substrate 45 and the multi-layer substrate 46 perpendicular to the optical axis direction of the solid state image sensor 44 in FIG. 7, the electronic component 57 is arranged between the image signal wiring pattern through which the image signal is transmitted and the drive signal wiring pattern through which the drive signal is transmitted, whereby a shield effect of the electronic component 57 can reduce noise to the image. While the electronic components 57 and 58 are arranged between the image signal wiring pattern through which the image signal is transmitted and the drive signal wiring pattern through which the drive signal is transmitted in the cross-section of the substrate 45 and the multi-layer substrate 46 perpendicular to the optical axis direction of the solid state image sensor 44 in the first embodiment, the noise to the image can be reduced by the shield effect when at least one electronic component is arranged between the image signal wiring pattern through which the image signal is transmitted and the drive signal wiring pattern through which the drive signal is transmitted in a part of the cross section of the substrate 45 and the multi-layer substrate 46 perpendicular to the optical axis direction of the solid state image sensor 44.

In the first embodiment, the drive signal electrode pad 38a-1 and the image signal electrode pad 38a-6 are formed to be farthest apart from each other so that the drive signal wiring pattern and the image signal wiring pattern connected are formed while separated on left and right sides in plan view to be able to secure a spatial distance between the image signal wiring pattern and the drive signal wiring pattern, and that the noise to the image can be reduced.

In the first embodiment, the image signal is output to the image signal cable 48B on the multi-layer substrate by the image signal wiring pattern on the surface of the multi-layer substrate 46 through the via hole 71 while the drive signal is transmitted from the drive signal cable 48A on the substrate 45 by the drive signal wiring pattern on the substrate 45 but, for example, it may also be adapted such that the image signal is transmitted only on the substrate 45 while the drive signal is transmitted mainly on the surface of the multi-layer substrate 46.

Figure 8:
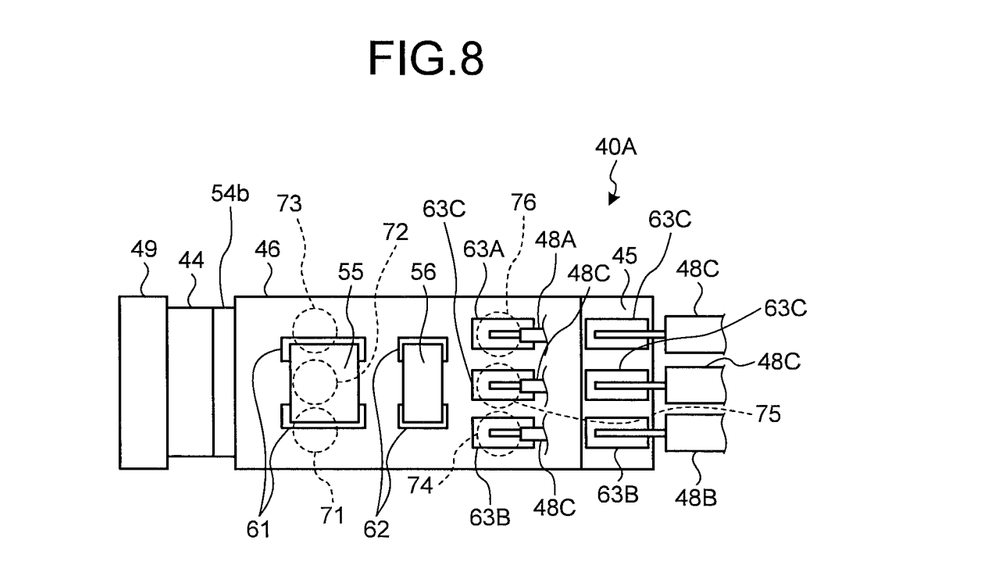
FIG. 8 is a plan view of an imaging module according to a first modification of the first embodiment as seen in plan view along a layered direction.

FIG. 8 is a plan view of an imaging module according to a first modification of the first embodiment as seen in plan view along a layered direction. In an imaging module 40A, a drive signal cable 48A is connected to a cable connection land 63A on the surface of a multi-layer substrate 46 while an image signal cable 48B is connected to a cable connection land 63B on a substrate 45.

According to the first modification, an image signal is transmitted from an image signal electrode pad 38a-6 of a solid state image sensor 44 to the substrate 45 through an inner lead, passes through only an image signal wiring pattern on the substrate 45, and is output to the image signal cable 48B. A drive signal input from the drive signal cable 48A connected to the surface of the multi-layer substrate 46 is input to a drive signal electrode pad 38a-1 through a drive signal wiring pattern on the multi-layer substrate 46 and a via hole 73. In the first modification, the via hole 73 is a first via hole closest to the solid state image sensor 44 so that the drive signal is transmitted through the via hole 73. An electronic component amplifying the image signal and including a transmission buffer is preferably mounted close to the image signal electrode pad 38a-6 on the substrate 45.

Similar to the first embodiment, according to the first modification, the electronic component or the like including the transmission buffer is arranged between the image signal wiring pattern through which the image signal is transmitted and the drive signal wiring pattern through which the drive signal is transmitted in at least a part of a cross section of the substrate 45 and the multi-layer substrate 46 perpendicular to the optical axis direction of the solid state image sensor 44, whereby a shield effect of the electronic component can reduce noise to an image.

Second Embodiment

Figure 9:
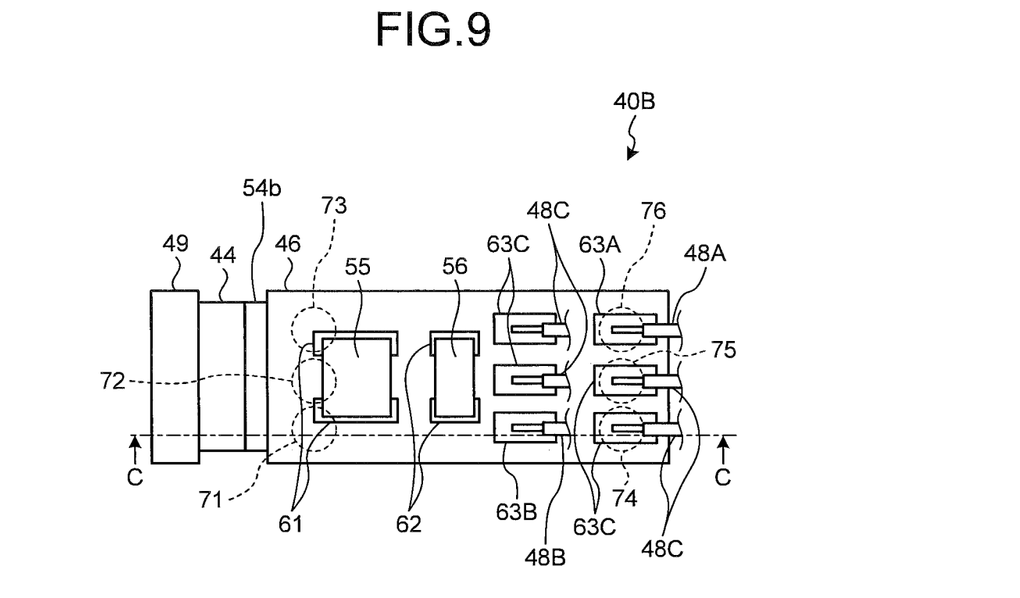
FIG. 9 is a plan view of an imaging module according to a second embodiment as seen in plan view along a layered direction.
Figure 10:
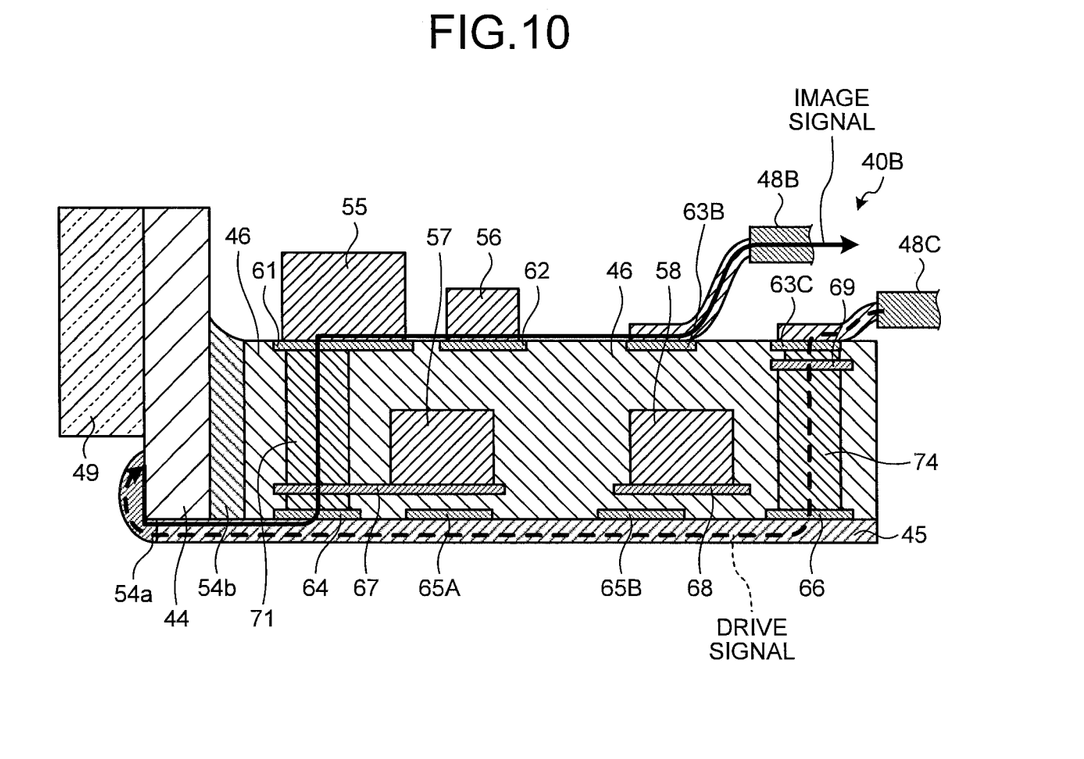
FIG. 10 is a cross-sectional view taken along line C-C of FIG. 9.

An imaging module according to a second embodiment is different from that of the first embodiment in that a drive signal cable 48A, an image signal cable 48B and a power supply cable 48C are connected on a multi-layer substrate 46. FIG. 9 is a plan view of the imaging module according to the second embodiment as seen in plan view along a layered direction. FIG. 10 is a cross-sectional view taken along line C-C of FIG. 9 and obtained when the imaging module is sectioned by a plane perpendicular to a surface of a substrate 45 and parallel to an optical axis direction of a solid state image sensor 44.

In an imaging module 40B of the second embodiment, as indicated with a solid line in FIG. 10, an image signal is transmitted to the image signal cable 48B as is the case with the first embodiment. On the other hand, as indicated with a dotted line in FIG. 10, a drive signal input from the drive signal cable 48A is transmitted to a drive signal wiring pattern formed on the substrate 45 through a cable connection land 63A and a via hole 76 and then input to a drive signal electrode pad 38a-1. In the second embodiment, the image signal is transmitted from the substrate 45 to an image signal wiring pattern on a surface of the multi-layer substrate 46 through a via hole 71, while the drive signal is transmitted from the multi-layer substrate 46 to the drive signal wiring pattern on the substrate 45 through the via hole 76. The drive signal and the image signal are transmitted through different layers (the image signal is mainly transmitted on the multi-layer substrate 46 while the drive signal is mainly transmitted on the substrate 45). In the second embodiment, the via hole 71 is a first via hole which is closest to the solid state image sensor 44 and through which the image signal is transmitted, whereas the via hole 76 is a second via hole which is arranged farthest from the solid state image sensor 44 and formed at the most distal position from the first via hole and through which the drive signal is transmitted.

The drive signal cable 48A, the image signal cable 48B and the power supply cable 48C are connected on the surface of the multi-layer substrate 46 in the imaging module 40B of the second embodiment, whereby soldering at the time of connection can be performed on a single site (performed once) to be able to improve workability. Moreover, as with the first embodiment, electronic components 57 and 58 are arranged between the image signal wiring pattern and the drive signal wiring pattern in the cross section of the substrate 45 and the multi-layer substrate 46 of the imaging module 40B perpendicular to the optical axis direction of the solid state image sensor 44, whereby a shield effect of the electronic components 57 and 58 can reduce noise to the image.

Figure 11:
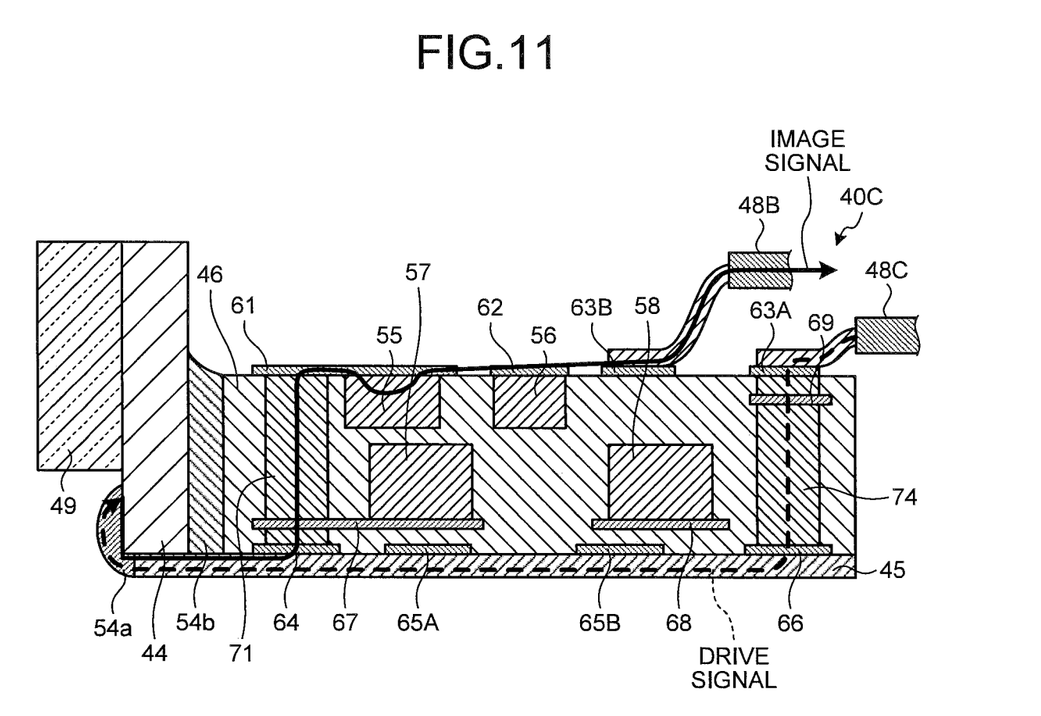
FIG. 11 is a cross-sectional view of an imaging module according to a first modification of the second embodiment.

All electronic components mounted on or in the multi-layer substrate 46 may be embedded inside the multi-layer substrate 46 as well. FIG. 11 is a cross-sectional view of an imaging module according to a first modification of the second embodiment and obtained when the imaging module is sectioned by a plane perpendicular to a surface of a substrate 45 and parallel to an optical axis direction of a solid state image sensor 44.

In an imaging module 40C according to the first modification of the second embodiment, electronic components 55, 56, 57 and 58 are embedded inside a multi-layer substrate 46.

In the imaging module 40C according to the first modification, as indicated with a solid line in FIG. 11, an image signal is transmitted from an image signal electrode pad 38a-6 of the solid state image sensor 44 to the substrate 45 through an inner lead and then transmitted to the electronic component 55 embedded inside the multi-layer substrate 46 through a connection land 64, a via hole 71, and a connection land 61. The image signal is amplified by the electronic component 55 and thereafter output to a processor 10 via an image signal wiring pattern, a cable connection land 63B and an image signal cable 48B on the multi-layer substrate 46.

On the other hand, as indicated with a dotted line in FIG. 11, a drive signal input from a drive signal cable 48A is transmitted to a drive signal wiring pattern formed on the substrate 45 through a cable connection land 63A and a via hole 76 and then input to a drive signal electrode pad 38a-1. In the imaging module 40C according to the first modification, the electronic components 55, 56, 57 and 58 are arranged between the image signal wiring pattern and the drive signal wiring pattern in the cross section of the substrate 45 and the multi-layer substrate 46 of the imaging module 40C perpendicular to the optical axis direction of the solid state image sensor 44, whereby a shield effect of the electronic components 55, 56, 57 and 58 can reduce noise to the image. Moreover, as with the second embodiment, the drive signal cable 48A, the image signal cable 48B and a power supply cable 48C are connected on the surface of the multi-layer substrate 46, whereby soldering at the time of connection can be performed on a single site (performed once) to be able to improve workability.

Alternatively, when the image signal cable is connected on the substrate 45 while the drive signal cable is connected on the multi-layer substrate 46 by forming the connection lands of the image signal cable 48B and the drive signal cable 48A on the substrate 45 and the multi-layer substrate 46, respectively, for the convenience of an arrangement space of the signal cable, the image signal is transmitted from the image signal electrode pad 38a-6 of the solid state image sensor 44 to the substrate 45 through the inner lead, transmitted to the electronic component 55 mounted (or embedded) on or in the multi-layer substrate 46 through the connection land 64, the via hole 71, and the connection land 61, amplified by the electronic component 55, and thereafter transmitted again to the substrate 45 through a via hole (such as a via hole 72) closest to the solid state image sensor 44 to be output to the processor 10 via the image signal cable 48B. On the other hand, the drive signal input from the drive signal cable 48A is transmitted to the drive signal wiring pattern formed on the substrate 45 through the cable connection land 63A and the via hole 76 and then input to the drive signal electrode pad 38a-1. With this configuration, even when the image signal cable 48B is connected to the substrate 45, it is possible to reduce noise in image by arranging the via hole through which the image signal is transmitted and the via hole through which the drive signal is transmitted most distant from each other while sandwiching the embedded electronic components.

According to some embodiments, since the electronic component is embedded inside the multi-layer substrate, it is possible to reduce interference between the image signal and the drive signal which are transmitted through different layers and thereby to suppress noise.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging module comprising:
   a solid state image sensor having a light-receiving surface, the solid state image sensor being configured to receive light and to convert the received light to an image signal;
   a substrate having a conductor layer and extending from the solid state image sensor in a direction opposite to where the light-receiving surface is provided, along an optical axis direction of the solid state image sensor;
   a multi-layer substrate disposed on a surface of the substrate, the multi-layer substrate having therein a plurality of conductor layers and a plurality of via holes, the plurality of conductor layers and the plurality of via holes being formed inside the multi-layer substrate, at least one electronic component being embedded inside the multi-layer substrate;
   an image signal electrode pad disposed on the solid state image sensor;
   a drive signal electrode pad disposed on the solid state image sensor;
   an image signal cable for transmitting the image signal;
   a drive signal cable for transmitting a drive signal;
   an image signal passage that electrically connects the image signal electrode pad and the image signal cable, the image signal passage being routed at least from the image signal electrode pad to the substrate; and
   a drive signal passage that electrically connects the drive signal cable and the drive signal electrode pad, the drive signal passage being routed at least from the drive signal electrode pad to the substrate;
   wherein either one of the image signal passage and the drive signal passage is diverted from the substrate to a conductor layer of the multi-layer substrate in a position between the solid state image sensor and the at least one electronic component embedded inside the multi-layer substrate, such that the image signal and the drive signal are transmitted to the image signal cable and the drive signal electrode pad, respectively, through the different conductor layers of the substrate and the multi-layer substrate.

2. The imaging module according to claim 1, wherein in a cross-sectional view of the substrate and the multi-layer substrate perpendicular to the optical axis direction of the solid state image sensor, the at least one of the plurality of electronic components is arranged between the image signal passage and the drive signal passage.

3. The imaging module according to claim 1, wherein the image signal or the drive signal is transmitted through a first via hole that is located closest to the solid state image sensor among the plurality of via holes.

4. The imaging module according to claim 1, wherein the drive signal cable is connected to the substrate, and the image signal cable to which the image signal is output is connected on the multi-layer substrate.

5. The imaging module according to claim 1, wherein the drive signal cable and the image signal cable are connected on the multi-layer substrate.

6. The imaging module according to claim 5, wherein
   the image signal is transmitted to the image signal cable connected on the multi-layer substrate through a first via hole that is located closest to the solid state image sensor among the plurality of via holes, and
   the drive signal input from the drive signal cable connected on the multi-layer substrate is transmitted through a second via hole that is located farthest away from the solid state image sensor and formed most distant from the first via hole among the plurality of via holes.

7. The imaging module according to claim 1, wherein
   a chip including at least a transmission buffer is mounted on the multi-layer substrate, and
   the image signal is transmitted to the image signal cable through the chip.

8. The imaging module according to claim 1, wherein
   the drive signal electrode pad and the image signal electrode pad are arranged separately from one another, and
   the image signal passage and the drive signal passage are arranged separately from one another in plan view from above.

9. The imaging module according to claim 1, wherein
   the image signal cable is connected on the multi-layer substrate, and
   a first via hole closest to the solid state image sensor among the plurality of via holes is located closest to the image signal electrode pad in plan view from above.

10. The imaging module according to claim 1, wherein the multi-layer substrate is a multi-layer resin substrate in which multiple resin substrates are layered.

11. An endoscope apparatus comprising an insertion unit, at a distal end of which the imaging module according to claim 1 is provided.

12. The imaging module according to claim 1, further comprising a cable connection land disposed on an upper surface of the multi-layer substrate, wherein one of the image signal cable and the drive signal cable is electrically connected to the cable connection land.

13. The imaging module according to claim 1, further comprising a connection land formed on a bottom surface of the multi-layer substrate, the connection land being electrically connected to the conductor layer of the substrate.

* * * * *